United States Patent [19]

Woodle

[11] 4,335,598
[45] Jun. 22, 1982

[54] UOP CHARACTERIZATION FACTOR MONITOR

[75] Inventor: Robert A. Woodle, Nederland, Tex.

[73] Assignee: Texaco Inc., White Plains, N.Y.

[21] Appl. No.: 127,665

[22] Filed: Mar. 6, 1980

[51] Int. Cl.³ ............................................. G01N 11/00
[52] U.S. Cl. ............................................. 73/53; 73/54
[58] Field of Search ............................ 73/53, 54, 32 R

[56] References Cited

U.S. PATENT DOCUMENTS 3,090,222  5/1963  Akaboshi et al. ..................... 73/53

Primary Examiner—Kyle L. Howell
Assistant Examiner—Joseph W. Roskos
Attorney, Agent, or Firm—Carl G. Ries; Robert A. Kulason; Ronald G. Gillespie

[57] ABSTRACT

A monitor which provides a signal corresponding to the Universal Oil Product (UOP) characterization factor of a hydrocarbon stream includes apparatus for sampling a portion of the hydrocarbon stream. Other apparatus changes the temperature of the sample to a predetermined temperature. A viscosity analyzer receives the sample and provides a signal corresponding to the viscosity of the hydrocarbon stream at the predetermined temperature. A refractometer receives the sample and provides a signal corresponding to the refractive index of the hydrocarbon stream at the predetermined temperature. An output network connected to the viscosity analyzer and to the refractometer provides the signal corresponding to the UOP characterization factor in accordance with the signals from the viscosity analyzer and the refractometer.

5 Claims, 1 Drawing Figure

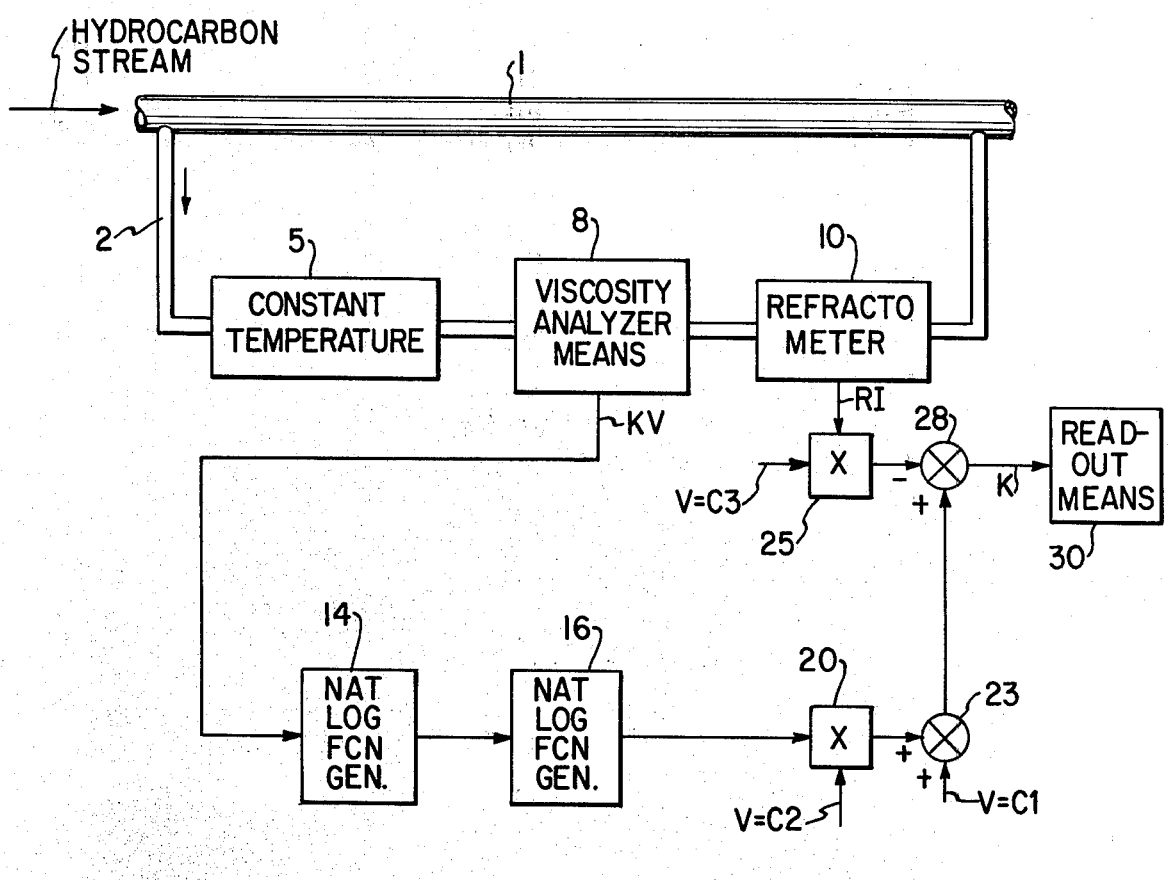

UOP CHARACTERIZATION FACTOR MONITOR

BACKGROUND OF THE INVENTION

Field of the Invention

The present invention relates to monitors in general and, more particularly, to monitors monitoring the UOP characterization factor of hydrocarbon stream.

SUMMARY OF THE INVENTION

The UOP characterization factor of a hydrocarbon stream is monitored by a monitor which includes apparatus for sampling the hydrocarbon stream and changing the temperature of the sample to a predetermined temperature. A viscosity analyzer analyzes the sample and provides a signal corresponding to the viscosity of the hydrocarbon stream at the predetermined temperature. A refractometer receives the sample and provides a signal corresponding to the refractive index of the hydrocarbon stream at the predetermined temperature. An output network connected to the analyzer and to the refractometer provides a signal corresponding to the UOP characterization factor of the hydrocarbon stream in accordance with the signals from the viscosity analyzer and the refractometer.

The object and advantages of the invention will appear more fully hereinafter, from a consideration of the detailed description which follows, taken together with the accompanying drawing, wherein one embodiment is illustrated by way of example. It is to be expressly understood, however, that the drawing is for illustrative purposes only and is not to be construed as defining the limits of the invention.

DESCRIPTION OF THE DRAWING

The drawing is a simplified block diagram of a monitor, constructed in accordance with the present invention, which provides a signal corresponding to the UOP characterization factor of a hydrocarbon stream.

DESCRIPTION OF THE INVENTION

Referring to the drawing, a hydrocarbon stream in a line 1 is sampled by a bypass line 2 which provides it to a conventional cooling device 5, which controls the temperature of the sample in line 2 to be at approximately 70° C. If the temperature of the stream is less than 70° C. then a heater would be used in place of device 5. The sample is then provided to a viscosity analzyer means 8 and to a refractometer 10 which provide signals KV and RI, respectively, corresponding to the kinematic viscosity in centistokes at 70° C. and refractive index at 70° C. of the hydrocarbon stream. The sample stream is returned to line 1. The UOP characterization factor K is determined from signals KV and RI, and the following equation:

$$K = C1 + C2 \ln\ln(KV) - C3(RI)$$

where C1, C2 and C3 are constants having preferred values of 42.3, 0.764 and 21.0, respectively.

Signal KV is applied to a conventional type natural log function generator 14 which provides a signal corresponding to the natural logarithm of signal KV to another natural log function generator 16, which provides a signal corresponding to the term lnln (KV) in the equation. The signal from natural log function generator 16 is multiplied with a direct current voltage, corresponding to the constant C2, by a multiplier 20. Multiplier 20 provides a product signal which is summed with another direct current voltage corresponding to the constant C1, by summing means 23, to provide a sum signal.

A multiplier 25 multiplies signal RI with a direct current voltage corresponding to the constant C3 to provide a signal which is subtracted from the signal provided by summing means 23 by subtracting means 28. Subtracting means 28 provides signal K, corresponding to the UOP characterization factor, to a readout device 30.

The present invention as hereinbefore described is a signal generator providing a signal corresponding to the UOP characterization factor K of a hydrocarbon stream in accordance with the kinematic viscosity and the refractive index of that stream at 70° C.

What is claimed is:

1. A UOP characterization factor monitor comprising means for sampling a hydrocarbon stream, means for changing the temperature of the sample hydrocarbon stream to a predetermined temperature, analyzer means receiving the sample hydrocarbon stream for providing a signal KV corresponding to the kinematic viscosity of the hydrocarbon stream at the predetermined temperature, refractometer means receiving the sample hydrocarbon stream for providing a signal RI corresponding to the refractive index of the hydrocarbon stream at the predetermined temperature, and output means connected to the analyzer means and to the refractometer means and receiving direct current voltages corresponding to constants C1, C2 and C3 for providing an output signal K corresponding to the UOP characterization factor in accordance with signals KV and RI, the received voltages, and the following equation $$K = C1 + C2 \ln\ln(KV) - C3(RI).$$

2. A monitor described in claim 1 in which the predetermined temperature is 70° C.

3. A monitor as described in claim 2 in which constants C1, C2 and C3 have preferred values of 42.3, 0.764 and 21.0, respectively.

4. A monitor as described in claim 1 in which the output means includes a first natural log function generator means connected to the viscosity analyzer means for providing a signal corresponding to the natural logarithm of the signal KV, a second natural log function generator connected to the first natural log function generator for providing signal corresponding to the natural logarithm of the natural logarithm of signal KV, a first multiplier connected to the second natural log function generator and receiving a direct current voltage corresponding to a value of constant C2 multiplies the signal from the second natural log function generator with the received voltage to provide a signal, summing means connected to the first multiplier and receiving a direct current voltage corresponding to a constant C1 for summing the received direct current constant C1 signal from the first multiplier to provide a sum signal, a second multiplier connected to the refractometer means and receiving a direct current voltage corresponding to a constant C3 multiplies the received voltage with signal RI to provide a product signal, and subtracting means connected to the summing means and to the second multiplier for subtracting the signal provided by the second multiplier from the signal provided by the summing means to provide signal K corresponding to the UOP characterization factor.

5. A monitor as described in claim 3 or 4 further comprising read-out means receiving signal K for providing a read-out of signal K.

* * * * *